United States Patent [19]

Georgopoulos

[11] Patent Number: 4,642,811
[45] Date of Patent: Feb. 10, 1987

[54] EXAFS SPECTROMETER

[75] Inventor: Panayotis Georgopoulos, Northbrook, Ill.

[73] Assignee: Northwestern University, Evanston, Ill.

[21] Appl. No.: 619,841

[22] Filed: Jun. 12, 1984

[51] Int. Cl.⁴ ............................................. G01N 23/08
[52] U.S. Cl. ........................................ 378/53; 378/75; 378/84
[58] Field of Search ...................... 378/71, 75, 82, 84, 378/73, 51, 53, 46

[56] References Cited

U.S. PATENT DOCUMENTS 3,903,414  9/1975  Herbstein et al. ............... 378/46
4,317,994  3/1982  Mallozzi et al. ................ 378/53

OTHER PUBLICATIONS

AIP Conference Proceedings, Laboratory EXAFS Facilities 1980 (University of Washington Workshop), edited by Edward A. Stern, American Institute of Physics, New York, 1980.
Knapp, G. S. and Georgopoulos, P., "EXAFS Study of Crystalline Materials", Crystals, Growth Properties and Applications 7, Springer-Verlag, Berlin, 1982.
Georgopoulos, P. and Knapp, G. S., "Design Criteria for a Laboratory EXAFS Facility", J. Appl. Cryst. 14, 3, (1981).

Primary Examiner—Carolyn E. Fields
Attorney, Agent, or Firm—Welsh & Katz, Ltd.

[57] ABSTRACT

An apparatus for performing extend X-ray absorption fine structure (EXAFS) measurements on materials. The EXAFS apparatus is constructed using a conventional X-ray powder diffractometer assembly with a rotating anode X-ray source affixed to the diffractometer assembly, a monochromator crystal rotatably positioned at the center of the assembly and a specimen stage and detectors slidingly mounted on a receiving track of the assembly. The monochromator crystal is automatically and elastically distorted to provide a monochromatic X-ray beam flux from the crystal. The angle of incidence of the source X-ray beam with the crystal surface is changed to provide a different monochromatic X-ray wavelength with changing energy, which enables measurement of the desired EXAFS spectra for the material.

40 Claims, 10 Drawing Figures

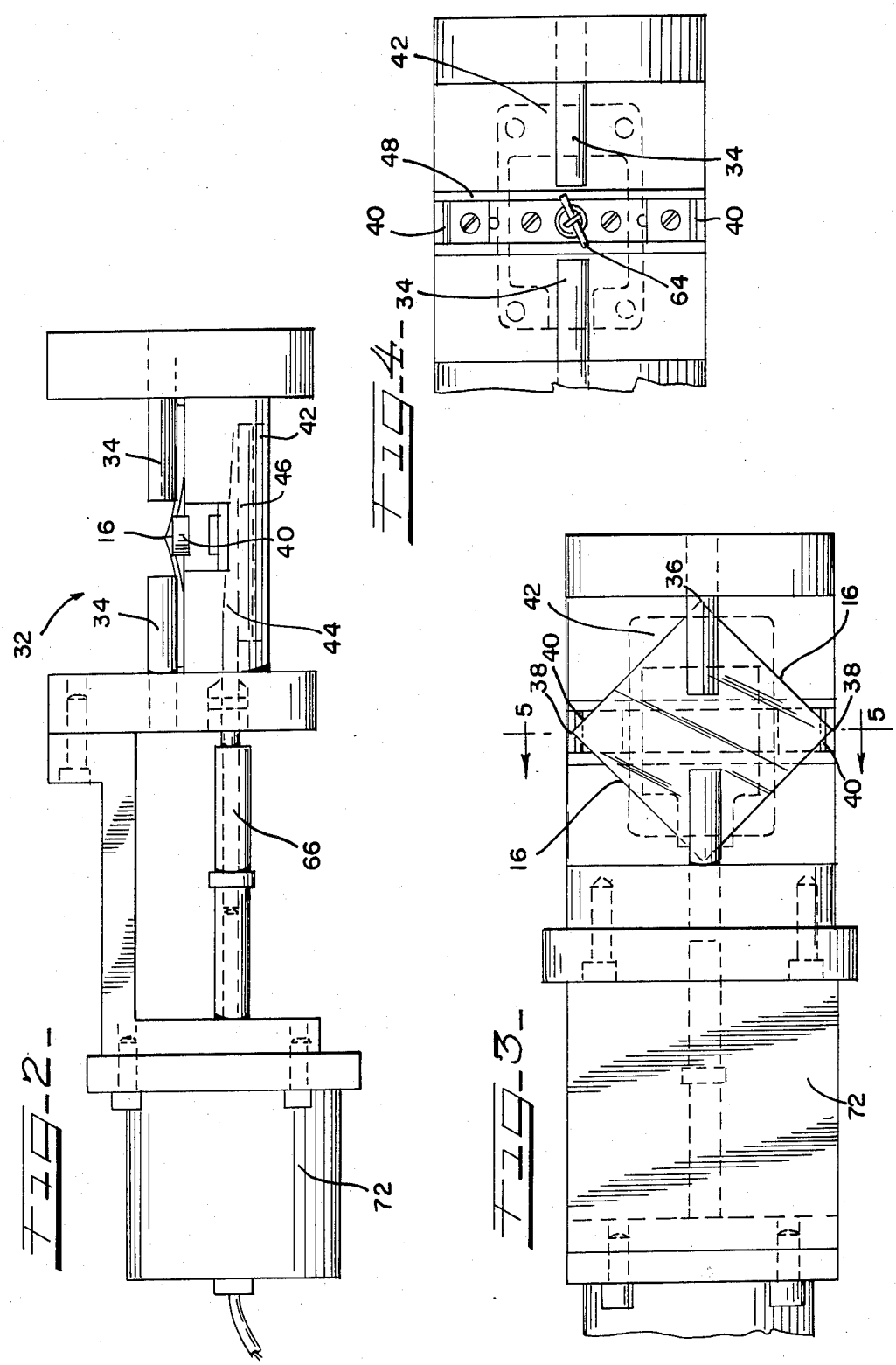

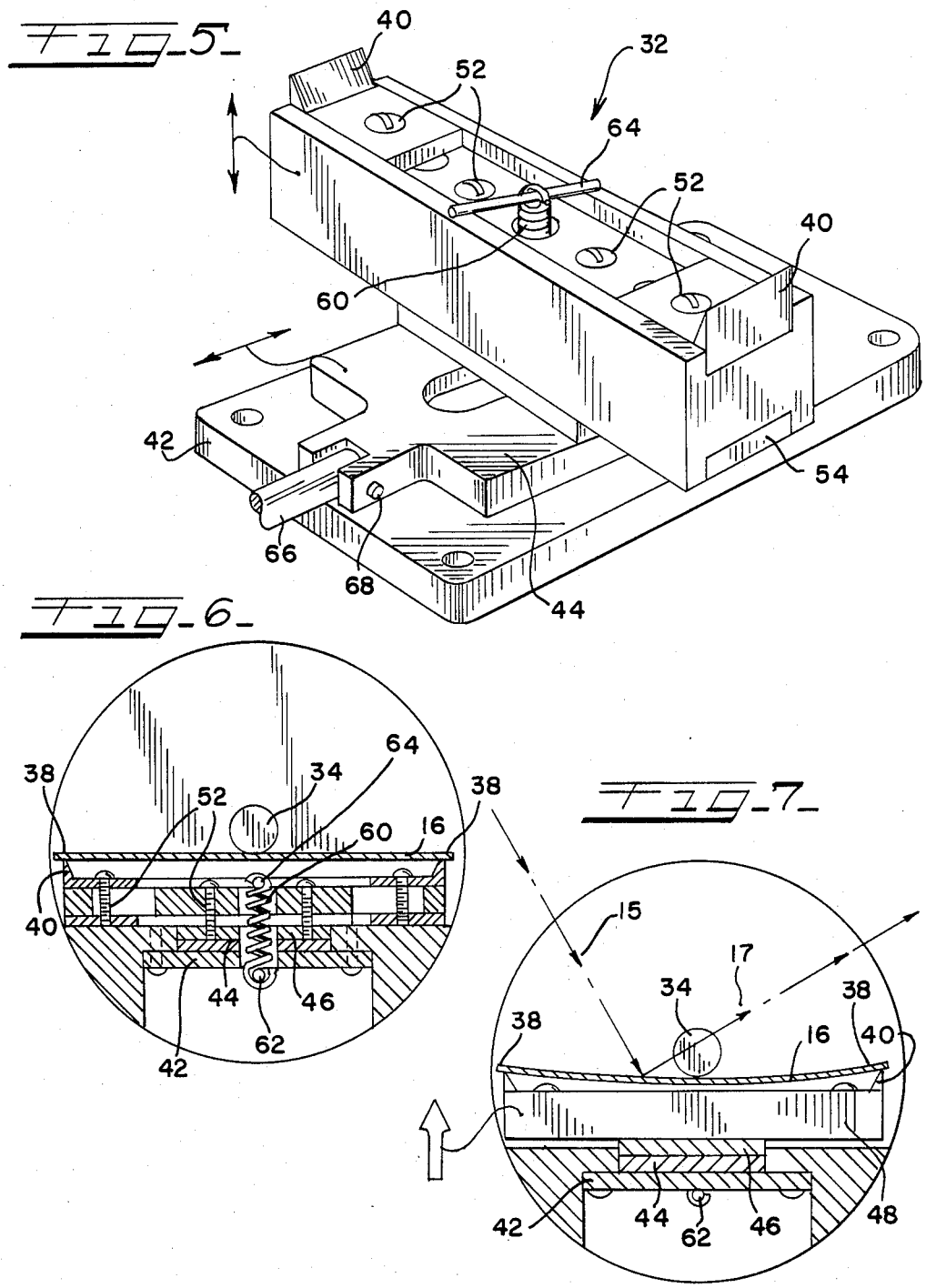

4,642,811

EXAFS SPECTROMETER

The present invention relates generally to a spectrometer for performing extended X-ray absorption fine structure (EXAFS) measurements on materials. More particularly, this invention relates to an apparatus for performing EXAFS measurements using an adaptation of a conventional X-ray powder diffractometer assembly to carry out the measurements using a set of predetermined operating conditions.

Investigation of the atomic level structural properties of materials has typically been performed by scattering experiments, which employ X-rays, neutrons or electrons, or alternatively by direct observation using sophisticated field ion microscopy or electron microscopy. More recently the technique of EXAFS has provided another important approach for the investigation of atomic and molecular level structure. The EXAFS method provides direct information on the types of atoms present and also identifies the number of atoms and the radial distance of atoms around an X-ray absorbing atom.

EXAFS measurements on materials have typically required the use of large, dedicated systems, such as synchrotron radiation sources. However, such systems are few in number, are expensive to operate and allow experimentation by user for only a few days a year. There has recently been development of compact laboratory scale EXAFS equipment. (See, for example, "Design Criteria for a Laboratory EXAFS Facility", J. Appl. Cryst. 14, 3 (1981), which is incorporated by reference herein). Unfortunately, such equipment is not adaptable to other tasks and tends to be quite expensive to construct.

Therefore, one of the object of the invention is to provide an improved apparatus for performing EXAFS measurements on a specimen.

A more particular object of the invention is to provide an improved apparatus for performing EXAFS measurements on a specimen by adapting a conventional X-ray powder diffractometer assembly to carry out a set of predetermined operating conditions to complete the EXAFS measurements.

Another object is to provide an improved EXAFS apparatus having a monochromator crystal which is automatically and elastically distorted in accordance with preselected distortion conditions to generate a focused monochromatic X-ray beam which changes wavelength as the angle of incidence of a source X-ray beam changes with respect to the crystal.

In accordance with the present invention, EXAFS measurements are performed on a specimen to investigate the local atomic structure. A standard X-ray diffractometer assembly is readily adapted to carry out the EXAFS measurements by following a set of predetermined opeating conditions. The apparatus is also conveniently changed back to function as an ordinary X-ray diffractometer apparatus. The apparatus includes an X-ray beam source, typically a rotating anode source, coupled to the diffractometer assembly, and a monochromator crystal rotatably positioned at the center of the diffractometer assembly. The monochromator crystal diffracts the source X-ray beam to produce a monochromatic X-ray beam, wherein the wavelength of the monochromatic beam changes as the angle of incidence of the source X-ray beam changes with respect to the crystal. This changing wavelength results in a changing X-ray energy which enables the measurement of the EXAFS spectrum as a function of energy.

In order to maintain optimum intensity and energy resolution for the monochromatic X-ray beam, the monochromator crystal is elastically distorted by a mechanical device under computer control. The monochromatic X-ray beam is directed toward a subject specimen supported by a specimen holder, which is slidingly positioned on a receiving track of the diffractometer assembly at an angle of twice the angle of incidence of the source X-ray beam with the crystal. The intensity of the variable-energy, monochromatic X-ray beam is then measured before and after passing through the specimen. A measure of the ratio of the incident to transmitted beam intensity in the vicinity of a selected one of the X-ray absorption edges enables evaluation of absorption coefficient fine structure (the EXAFS spectrum) as a function of energy and in turn allows evaluation of the characteristic local atomic order in the specimen.

Further objects and advantages of the present invention, together with the organization and manner of operation thereof, will become apparent from the following detailed description of the invention when taken in conjunction with the accompanying drawings, wherein like reference numerals designate like elements throughout the several views.

BRIEF DESCRIPTION OF THE DRAWINGS

FIG. 2 is an elevation view of a distortion fixture and coupled motor drive;

FIG. 3 is a top view of the distortion fixture and motor drive with a monochromator crystal in position on the fixture;

FIG. 4 is a top view of the end portion of the distortion fixture with the crystal removed from the fixture;

FIG. 5 is a perspective view of the distortion fixture and a coupled base plate;

FIG. 6 is an end view of the distortion fixture take along line 6—6 and showing the crystal in an undistorted state;

FIG. 7 is the same end view as in FIG. 6 but with the crystal in a distorted state;

DETAILED DESCRIPTION

Figure 1:
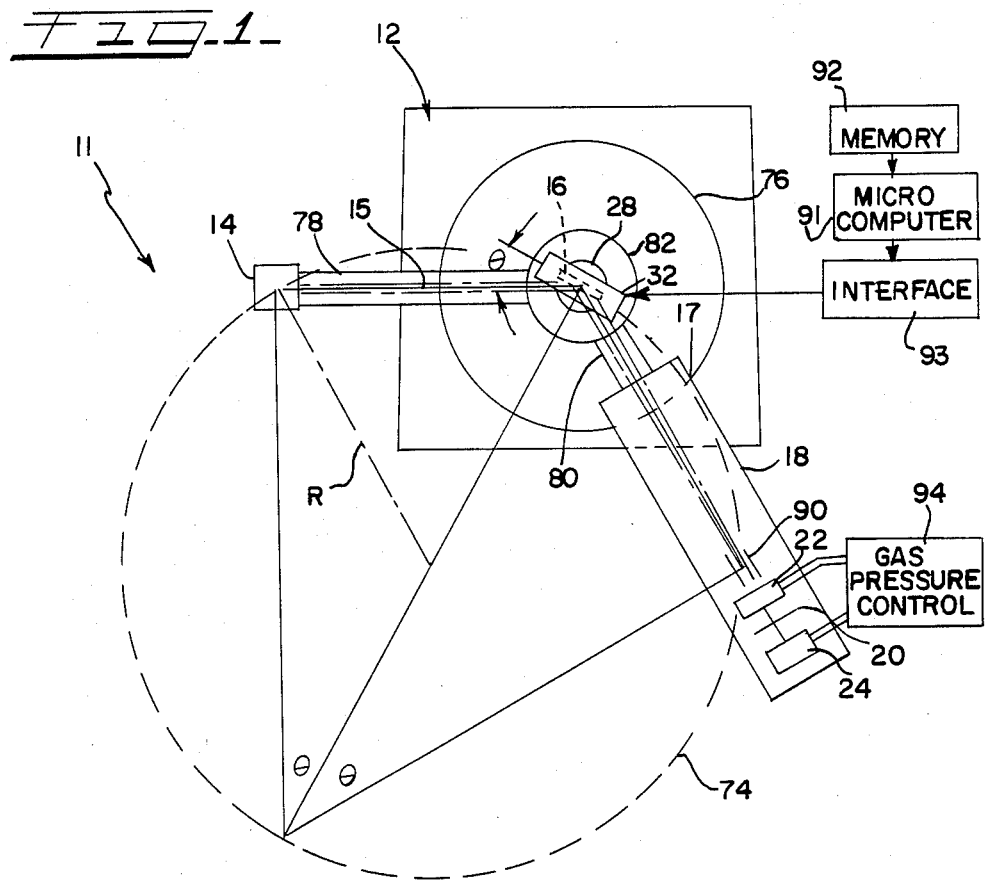
FIG. 1 is a top view of an EXAFS apparatus constructed in accordance with one embodiment of the present invention.

Referring now to the drawings and in particular to FIG. 1, an EXAFS apparatus constructed in accordance with one embodiment of the present invention is indicated generally at 11. Various components of the EXAFS apparatus 11 are supported by an X-ray assembly 12 which in a preferred embodiment is an adaptation of an X-ray powder diffractometer assembly as shown in FIG. 1. Very generally, the EXAFS components include X-ray source means, such as a rotating anode X-ray source 14, for providing a source X-ray beam 15 and a monochromator crystal 16 for providing a monochromatic X-ray beam 17 from the source X-ray beam 15. Also included is a stage means, such as specimen holder 18 which supports a specimen 20; and a detector means, such as X-ray detectors 22 and 24, which are used to measure the X-ray beam intensities incident upon and transmitted from, respectively, the specimen 20. In EXAFS measurements the incident and transmitted intensities are used to determine the X-ray absorption coefficient changes in the vicinity of a major absorption edge, i.e., the EXAFS or extended X-ray absorption fine structure. Analysis of these changes in the fine structure is used to characterize local atomic order in the specimen 20.

Turning now to a more detailed description of the EXAFS apparatus 11 shown in FIG. 1, the rotating anode X-ray source 14 is fixed with respect to the X-ray powder diffractometer assembly 12 (hereinafter assembly 12) to provide the source X-ray beam 15. This source X-ray beam 15 has a high flux, typically $10^6$ to $10^7$ counts/second, which is about 5 to 20 times that of a sealed X-ray tube unit. In a preferred form of the invention, the X-ray source 14 is affixed directly to the asssembly 12 in a manner to enable quick removal. Alternatively, the X-ray source 14 can be permanently attached to the assembly 12 or held in place apart from the assembly 12. The rotating anode X-ray source 14 typically has an anode constructed of a noble metal or refractory metal, such as gold, molybdenum, silver or tungsten. The monochromator crystal 16 is positioned on a motor driven, rotatable platform 28 located at the center of the assembly 12. The platform 28 is designed to easily replace a rotatable specimen holder normally located at the center of the assembly 12. Further, the motor drive mechanism for rotating the platform 28 can be used to rotate the platform 28, whether EXAFS or conventional X-ray diffraction measurements are being performed.

To carry out the EXAFS measurements, the monochromator crystal 16 is oriented at a selected angle of incidence with respect to the source X-ray beam 15. At the selected angle of incidence the diffracting planes of the monochromator crystal 16 scatter the incident X-ray beam 15 in accordance with Bragg's Law of diffraction to provide the diffracted monochromatic X-ray beam 17. The choice of the monochromator crystal 16 is usually dictated by energy resolution and by efficiency of scattering (See, J. Appl. Cryst. 14, 3 (1981) cited hereinbefore). Examples of acceptable materials for the crystal 16 are germanium, silicon, and lithium fluoride.

To optimize intensity and energy resolution of the monochromatic X-ray beam 17, a deforming means, such as a distortion fixture 32 shown in FIGS. 2-8, is used to elastically distort the monochromator crystal 16. As the crystal 16 rotates with respect to the incident source X-ray beam 15, the distortion fixture 32 applies a selected force to the crystal 16 to bend the shape into an appropriate predetermined cylindrical shape. Since the source X-ray beam 15 diverges from the X-ray source 14, the X-ray beam 15 includes X-rays with a range of different angles of incidence on the crystal 16. Therefore, by applying the selected force and forming the curved cylindrical surface for the crystal 16, the Bragg Law condition is satisfied for the largest possible portion of the crystal 16, providing optimum intensity and energy resolution for the diffracted monochromatic X-ray beam 17.

The selected amount of force applied to deform the monochromatic crystal 16, and the amount of consequent crystal distortion, is controlled by computer means, such as a microcomputer 91 or a microprocessor with associated memory 92. The microcomputer 91 provides this control by executing program means, such as computer software in a read only memory (ROM) or control information stored in a random access memory (RAM), each able to provide the characteristic preselected distortion conditions. Therefore, as the angle of the source X-ray beam 15 with respect to the crystal 16 changes due to the angular rotation of the monochromator crystal 16, the microcomputer outputs the preselected distortion conditions to the deforming means for execution.

Referring to FIGS. 2-8, the monochromator crystal 16 is held in the distortion fixture 32 by knife edges 40 and by restraining means, such as retaining pins 34. These retaining pins 34 are in contact with one face of the crystal 16 on a diagonally opposite first pair of corners 36 of the crystal 16. In the preferred embodiment, the crystal 16 is a diamond shaped thin slab with four corners. The crystal 16 is also held in position and elastically distorted by the knife edges 40 in contact with a second pair of diagonally opposite corners 38 and a predetermined force is applied to the knife edges 40 which results in elastic distortion of the crystal 16.

Figure 8:
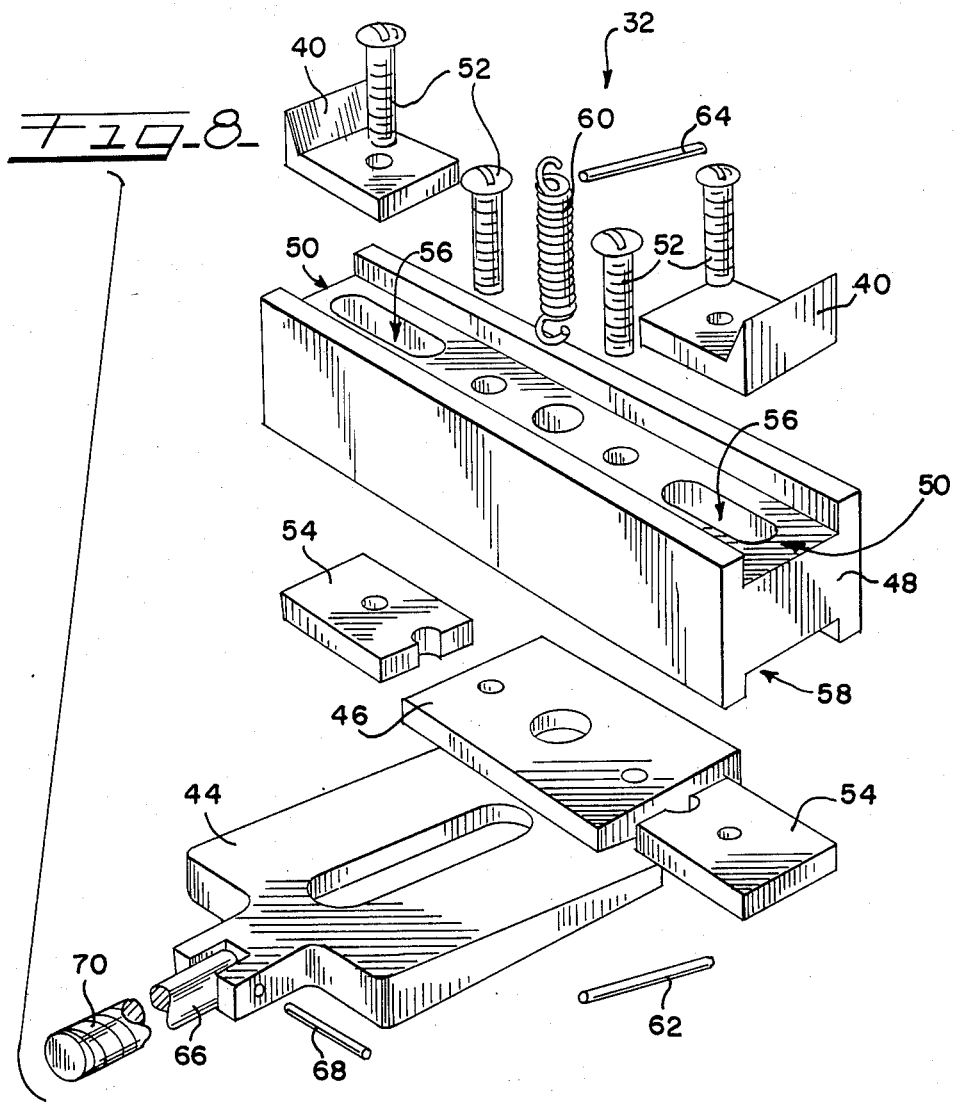
FIG. 8 is an exploded view in perspective of the distortion fixture shown in FIG. 5.
Figure 9:
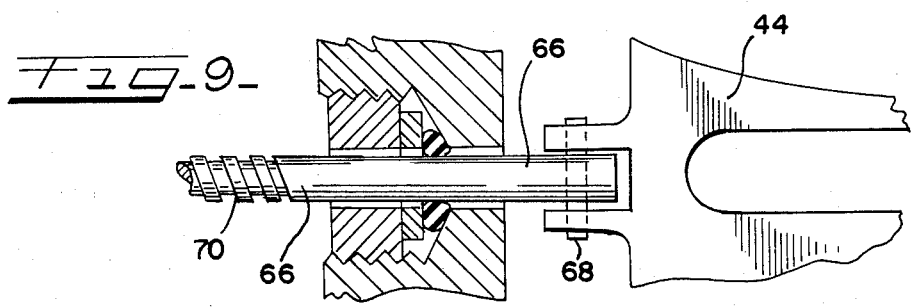
FIG. 9 is a partial cross sectional view of a sliding wedge coupled to a movable shaft.

In a preferred form of the invention, the distortion fixture 32 is shown generally in FIGS. 2-4 and in detail in FIGS. 5-9. The fixture 32 includes a base plate 42, a sliding wedge 44 having an inclined upper surface, as best shown in FIG. 8, a fixed wedge 46 and a support block 48 which holds the knife edges 40. As shown in the exploded view of FIG. 8, the knife edges 40 are positioned within the channel 50 of the support block 48 by bolts 52 threadedly engaged with holes in slot plates 54. Since the support block 48 has slotted bolt passageways 56, and the slot plates 54 are adjustably positionable along channel 58, the knife edges 40 can be adjusted to various locations along the channel 50 to accommodate individual crystals 16 of different sizes. The knife edges 40 and the support block 48 are held in position with respect to the base plate 42 by a spring 60. As shown in FIGS. 5-7, a lower pin 62 is used to fixedly restrain one end of the spring 60, and an upper pin 64 is used to fixedly restrain the other end of the spring 60 with respect to the base plate 42. As a consequence of the spring tension, the fixture 32 is firmly held together.

The fixture 32 changes the force applied to the crystal 16 by moving the sliding wedge 44 between the base plate 42 and the fixed wedge 46. This movement of the sliding wedge 44 causes the support block 48 and the knife edges 40 to move up or down depending on the drive direction for the sliding wedge 44. Consequently, the knife edges 40 distort the crystal 16 by pushing against and moving the second pair of corners 38 of the crystal 16. This effect is shown diagrammatically in FIGS. 6 and 7, wherein the crystal 16 is substantially undistorted in FIG. 6 and is shown distorted into a dished shape in FIG. 7.

As best shown in FIG. 5, movement of the sliding wedge 44 is accomplished by translating a movable shaft 66 which is coupled to the wedge 44 by a pin connection 68. The shaft 66 drives the sliding wedge 44 along the axial direction of the shaft 66 by means of a threaded portion 70 engaged with a rotatable gear coupling (not shown) which is turned by a motor drive (not shown) within housing 72.

Control of the distortion fixture 32 is accomplished by the motor drive mechanism controlled by a microcomputer 91 which executes the preselected set of distortion conditions stored in the computer memory. The microcomputer 91 outputs these distortion conditions as drive outputs to the motor drive by means of an interface means 93, such as a digital to analog converter. In turn, the motor drive operates the sliding wedges 44 to apply the force through the knife edges 40 to each of the second pair of corners 38 of the crystal 16. The movement of the wedge 44 enables continuous adjustment of the radius of curvature for the crystal 16, allowing conformance to a Rowland circle 74 (shown in FIG. 1) which changes as the diffractometer radius R and scattering angle $\theta$ changes. In a manner known to one skilled in the art, by conforming to the Rowland circle 74, the optimum scattering intensity and energy resolution are maintained for the monochromatic X-ray beam 17 provided from the monochromator crystal 16.

After scattering from the monochromator crystal 16, the diffracted monochromatic X-ray beam 17 is directed toward the specimen 20. The specimen holder 18 supports the specimen 20 and is in sliding engagement with a receiving track 76 of the assembly 12. Throughout the EXAFS measurements the specimen 20 is rotated to a position located at an angle $2\theta$ (FIG. 1), which is twice the angle of incidence $\theta$ of the source X-ray beam 15 with the surface of the monochromator crystal 16. The angular rotation of both the crystal 16 and the specimen holder 18 is under the control of the microcomputer 91 which executes a set of predetermined operating conditions stored in the computer memory. It is also important to note that the rotational motion of the crystal 16 and the specimen holder 18 during the EXAFS measurements is precisely the same as that used in normal $\theta - 2\theta$ X-ray diffraction experiments on the assembly 12. This feature therefore readily enables change of the apparatus between the EXAFS and X-ray diffraction operational modes.

Figure 10:
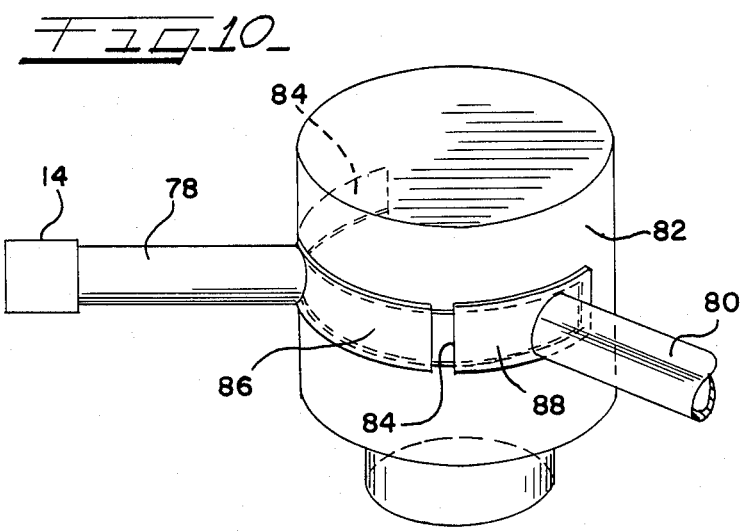
FIG. 10 is a crystal housing and associated cover housings used to enclose the crystal and X-ray beam path.

The path of the source X-ray beam 15 and the monochromatic X-ray beam 17 is substantially enclosed by beam path housings 78 and 80 shown in FIGS. 1 and 10, which help to prevent radiation exposure to an expeimenter or an observer. As shown generally in FIG. 1, and in detail in FIG. 10, the monochromator crystal 16 is also covered by a crystal housing 82. In a preferred embodiment the crystal housing 82 has a horizontally positioned slot 84 which enables the entry into and exit from the housing 82 of the source X-ray beam and the monochromatic X-ray beam 17, respectively. Attached to the beam path housings 78 and 80 are horizontal slot covers 86 and 88, respectively, which help contain the X-rays within the crystal housing 82 as the EXAFS measurements are taken. The slot covers 86 and 88 are positioned with respect to one another to result in covering the slot 84 at all angles of operation.

As shown in FIG. 1, the specimen holder 18 supports the specimen 20 and the detectors 22 and 24. The monochromatic X-ray beam 17 is directed toward the detectors 22 and 24 through slits 90 which act to prevent passage of any stray radiation to the detectors 22 and 24. The detectors 22 and 24 are positioned to measure the intensity of the monochromatic X-ray beam 17 before and after, respectively, passing through the specimen 20. Various detectors are usable for performing EXAFS measurements on the apparatus 11, including ion chamber detectors and proportional counters. In a preferred embodiment conventional proportional counters are used.

The entrance and exit windows of the proportional counters are made transparent to X-rays by using aluminized polyethylene terephthalate sold under the trademark name Mylar (a trademark of DuPont Corporation) or beryllium metal foil windows. In order to obtain the optimum statistics, and thus the smallest measuring error, the ratio of incident X-ray intensity to transmitted intensity is adjusted by changing the sensitivity of the two proportional counters (the detectors 22 and 24). The detector sensitivity is varied by means 94 for changing the gas pressure within the sealed proportional counters. The gas pressure can be controlled by a conventional gas flow monitor connected to high purity gas supplies in a manner known to one of ordinary skill in the art. The gases within the detectors 22 and 24 are typically argon and methane, and in a preferred embodiment the pressure is adjusted in the incident beam detector 22 to absorb approximately ten to twenty percent of the X-ray beam. The amount of X-ray beam intensity, $I_d$, detected by the incident beam detector 22 is, $$I_d = I_o(1-t)$$

where t is the fraction of intensity transmitted through the incident beam detector 22, and $I_o$ is the total incident beam intensity. After transmission through the specimen 20, the transmitted intensity is, $$I_t = I_o e^{-\mu x}$$

where $\mu$ is the linear absorption coefficient and x is the specimen thickness. Therefore in terms of the experimentally measure intensities, $I_d$ and $I_t$, $$\mu x = -\ln(I_t/I_d) + \ln[t/(1-t)]$$

and since $\ln[t/(1-t)]$ varies slowly with energy, it is not necessary to measure t with high accuracy to determine $\mu x$. From a measure of $\mu x$ one is able to determine the change of the absorption coefficient, $\mu$, as a function of energy in the vicinity of the X-ray absorption edge and therefore perform EXAFS analysis to characterize the local atomic order. (See, for example, *Laboratory EXAFS Facilities—1980 University of Washington Workshop*, American Institute of Physics, Proc. No. 64, 1980, which is incorporated by reference herein).

In a preferred form of the invention the X-ray detectors 22 and 24 are also able to discriminate against higher energy harmonics of the desired X-ray wavelength provided by the monochromator crystal 16. These components of $\lambda/n$ (where n is an integer greater than or equal to 2) arise from operating the X-ray source at voltages such that not only is the first order wavelength produced, but also $\lambda/2$, $\lambda/3$, etc. The shortest $\lambda/n$ is determined by the operating voltage of the X-ray source. These higher energy, shorter wavelength X-rays interact in a different manner than the desired X-ray wavelength and therefore are a source of error in evaluation and interpretation of the EXAFS measurements. In a preferred detector system, the transmitted X-ray beam detector 24 is constructed to have a diameter four times larger than the incident beam detector 22, and both of the detectors are operated at equal gas pressure. When the absolute gas pressure is adjusted such that the incident beam detector 22 attenuates ten percent of the incident beam 15, the transmitted beam detector 24 is only about thirty-five percent efficient. However, at the same time, the efficiency of the detector for higher order harmonics (or shorter wavelengths) is extremely low since the detector efficiency decreases as the third power of the X-ray energy. Any residual higher order wavelength harmonics can be eliminated electronically by electronic pulse height discriminators in a known manner.

The overall response of the currently available counter electronics is adequate up to about $3 \cdot 10^5$ counts/second, although linearity suffers at count rates above approximately $10^5$ counts/second. This problem would not be serious if the measured intensity varied only a small fraction of the average intensity. However, the presence of characteristic X-ray lines and impurity X-ray lines in the X-ray beam source usually results in large percentage flux changes as the X-ray wavelength is varied during performance of the EXAFS measurements. To compensate for these variations in X-ray source beam flux, a current controller can be utilized in a generator segment of a feedback loop to maintain at a constant value the output signal from the incident beam detector. (See, for example, J. Appl. Cryst. 14, 3 (1981) which has been cited hereinbefore).

The subject invention has important advantages over previous EXAFS apparati. These advantages include the ability to perform EXAFS measurements on a conventional X-ray diffractometer assembly which can also be used for ordinary X-ray diffraction measurements. The EXAFS measurements are readably performed as a function of incident X-ray energy which is changed by rotating the monochromator crystal 16 with respect to the source X-ray beam 15 to provide a changing X-ray wavelength. An optimized X-ray flux and energy resolution is obtained by continuously and elastically distorting the monochromator crystal 16 by the microcomputer controlled distortion fixture 32. The microcomputer 91 control also effects rotation of the monochromator crystal 16, the detectors 22 and 24 and the specimen 20, enabling completely automated EXAFS measurements. The microcomputer also is adaptable to control the unit when used in the ordinary X-ray diffraction experimental mode. Furthermore, the apparatus can be used to provide a selectable wavelength monochromatic X-ray beam for performance of a variety of additional experiments requiring monochromatic X-rays of different energy, such as, X-ray fluorescence measurements, X-ray diffraction as a function of X-ray energy, radiation damage experiments and other X-ray spectroscopy measurements.

While preferred embodiments of the present invention have been illustrated and described, it will be understood that changes and modifications may be made therein without departing from the invention in its broader aspects. Various features of the invention are defined in the following claims.

What is claimed is:

1. An apparatus for performing X-ray absorption fine structure measurements on a specimen by using a source X-ray beam and an assembly adapted to carry out a set of predetermined operating conditions, comprising:
   a monochromator crystal means rotatably positioned at the center of said assembly for diffracting said source X-ray beam to provide a monochromatic X-ray beam for selected angles of incidence of said source X-ray beam with respect to said crystal means, and in accordance with said predetermined operating conditions said crystal means providing said monochromatic X-ray beam having a different wavelength upon changing to a different respective associated one of said angles of incidence;
   deforming means for automatically distorting said monochromator crystal means at said angles of incidence to provide said monochromatic X-ray beam having said different wavelength at said respective associated angles of incidence;
   detector means for measuring the intensity of said monochromatic X-ray beam before and after passing through said specimen; and
   stage means for supporting said specimen and said detector means, said stage means being slidingly engaged with a receiving track of said assembly to enable movement on said track to an angular position twice that of said respective associated angle of incidence of said X-ray beam with said crystal means.

2. The apparatus as defined in claim 1 further including X-ray means for providing said source X-ray beam, said X-ray means being fixed with respect to said assembly.

3. The apparatus as defined in claim 2 wherein said X-ray means is affixed directly to said assembly.

4. The apparatus as defined in claim 2 wherein said X-ray means comprises a rotating anode X-ray generator.

5. The apparatus as defined in claim 4 wherein said rotating anode is composed of a material selected from the group consisting of gold, molybdenum, silver and tungsten.

6. The apparatus as defined in claim 1 wherein said assembly comprises an X-ray powder diffractometer assembly.

7. The apparatus as defined in claim 6 further characterized in that said monochromator crystal means comprises a relatively thin diamond shaped single crystal and said deforming means comprises a distortion fixture having a support structure including restraining pieces for holding one side of said crystal at a first pair of diagonally opposite corners thereof and for pushing against the side opposite said one side at a second pair of diagonally opposite corners of said crystal, the corners of said first pair being different from the corners of the second pair.

8. The apparatus as defined in claim 7 wherein said distortion fixture comprises a support structure having restraining pieces positioned against a first pair of diagonally opposite corners of said crystal.

9. The apparatus as defined in claim 7 wherein each of said restraining pieces comprises a retaining pin in contact with each of said first pair of diagonally opposite corners of said crystal.

10. The apparatus as defined in claim 7 further including computer means for providing preselected distortion conditions for instructing said deforming means to elastically distort said crystal.

11. The apparatus as defined in claim 10 wherein said computer means comprises a microprocessor.

12. The apparatus as defined in claim 11 wherein said computer means is couplable to interface means for providing a drive output to a motor drive for operating said deforming means.

13. The apparatus as defined in claim 1 wherein said deforming means selectively and elastically distorts said crystal means to a predetermined cylindrical shape to provide optimal intensity and energy resolution for said monochromatic X-ray beam at each of said respective associated angles of incidence.

14. The apparatus as defined in claim 13 wherein said distortion fixture comprises knife edge means for pushing against said second pair of diagonally opposite corners of said crystal means and motor driven slidign wedges disposed beneath said crystal means and sliding against a stationary backplate to exert a predetermined force on each of said knife edge means.

15. The apparatus as defined in claim 14 wherein said distortion fixture comprises a support structure having restraining pieces positioned against a first pair of diagonally opposite corners of said crystal means.

16. The apparatus as defined in claim 15 wherein each of said restraining pieces comprises a retaining pin in contact with each of said first pair of diagonally opposite corners of said crystal means.

17. The apparatus as defined in claim 14 further including computer means for providing preselected distortion conditions for instructing said deforming means to elastically distort said crystal means.

18. The apparatus as defined in claim 17 wherein said computer means comprises a microcomputer.

19. The apparatus as defined in claim 18 further including memory means couplable to said microcomputer for storing said preselected distortion conditions.

20. The apparatus as defined in claim 18 wherein said computer means is couplable to interface means for providing a drive output to a motor drive for moving said sliding wedges.

21. The apparatus as defined in claim 1 wherein said monochromator crystal means is selected from the group consisting of single crystals of silicon, germanium, and lithium fluoride.

22. The apparatus as defined in claim 1 wherein said detector means comprises at least one proportional counter.

23. The apparatus as defined in claim 22 wherein said detector means comprises a first proportional counter positioned to detect said monochromatic X-ray beam before passing through said specimen and a second proportional counter positioned to detect said monochromatic X-ray beam after passing through said specimen, said detector means further including means for chaging gas pressure within said first and said second proportional counters for optimizing counting statistics for a ratio of transmitted to incident X-ray beam intensity.

24. The apparatus as defined in claim 1 wherein said detector means comprises at least one ion chamber counter.

25. The apparatus as defined in claim 24 wherein said ion chamber counter comprises a first ion chamber counter positioned to detect said monochromatic X-ray beam before passing through said specimen and a second ion chamber counter positioned to detect said monochromatic X-ray beam after passing through said specimen.

26. An apparatus for performing X-ray absorption fine structure measurements on a specimen by adapting an X-ray powder diffractometer assembly to carry out a set of predetermined operating conditions, comprising:
 a rotating anode X-ray beam source affixed to said diffractometer assembly;
 a diamond shaped single crystal means rotatably positioned at the center of said diffractometer assembly for diffracting said source X-ray beam to provide a monochromatic X-ray beam for selected angles of incidence of said source X-ray beam with respect to said crystal means, and in accordance with said predetermined operating conditions, said crystal means providing said monochromatic X-ray beam having a different wavelength upon changing to a different respective associated one of said angles of incidence;
 deforming means for automatically and elastically distorting said monochromator crystal means at each of said angles of incidence to provide said monochromatic X-ray beam having said different wavelength at each of said respective associated angles of incidence;
 a first and second proportional counter positioned to detect said monochromatic X-ray beam, before and after, respectively, passing through said specimen; and
 stage means for supporting said specimen and said proportional counters, said stage means slidingly engaged with a receiving track of said diffractometer assembly to enable movement on said track to an angular position twice that of said respective associated angle of incidence of said X-ray beam with said crystal means.

27. The apparatus as defined in claim 26 wherein said rotating anode is composed of a material selected from the group consisting of gold, molybdenum, silver and tungsten.

28. The apparatus as defined in claim 26 wherein said deforming means comprises a distortion fixture having restraining pieces positioned against a first pair of diagonally opposite corners of said crystal means.

29. The apparatus as defined in claim 28 wherein each of said restraining pieces comprises a retaining pin in contact with each of said first pair of diagonally opposite corners of said crystal means.

30. The apparatus as defined in claim 26 wherein said deforming means comprises knife edge means for pushing against a second pair of diagonally opposite corners of said crystal means and sliding wedges disposed beneath said crystal means and sliding against a stationary backplate to exert a predetermined force on each of said knife edge means.

31. The apparatus as defined in claim 30 wherein said deforming means further includes retaining pins positioned against a first pair of diagonally opposite corners of said crystal means.

32. The apparatus as defined in claim 26 further including computer means for providing preselected distortion conditions for instructing said deforming means to elastically distort said crystal means.

33. The apparatus as defined in claim 32 wherein said computer means comprises a microprocessor.

34. The apparatus as defined in claim 33 further including memory means couplable to said microprocessor for storing said set of predetermined operating conditions and said preselected distortion conditions.

35. The apparatus as defined in claim 34 wherein said computer means is couplable to interface means for providing a drive output to a motor drive for operating said deforming means.

36. The apparatus as defined in claim 26 wherein said crystal means is selected from the group consisting of single crystals of silicon, germanium and lithium chloride.

37. The apparatus as defined in claim 26 further including means for changing gas pressure within said first and said second proportional counters for optimizing counting statistics for a ratio of transmitted to incident X-ray beam intensity.

38. A method of performing EXAFS measurements on a specimen by adapting an X-ray powder diffractometer assembly to carry out a set of predetermined operating conditions, comprising:

providing a source X-ray beam by operating an X-ray source;

positioning a monochromator crystal on a rotatable crystal holder disposed at the center of said diffractometer assembly;

diffracting said source X-ray beam from said monochromator crystal to provide a monochromatic X-ray beam for selected angles of incidence of said source X-ray beam with respect to said crystal, and in accordance with said predetermined operating conditions said crystal providing said monochromatic X-ray beam having a different wavelength upon changing to a different respective associated one of said selected angles of incidence of said source X-ray beam with respect to said crystal;

distorting automatically and elastically said monochromator crystal at each of said angles of incidence to provide said monochromatic X-ray beam having said different wavelength at each of said respective associated angles of incidence;

detecting with X-ray detectors said monochromatic X-ray beam before and after passing through said specimen;

rotating said monochromator crystal to a next one of said angles of incidence to provide said different wavelength; and moving said specimen and said X-ray detector along a receiving track of said diffractometer assembly to an angular position twice that of said next one of said angles of incidence of said X-ray beam with said crystal.

39. An apparatus adapted for use for EXAFS measurements, said apparatus adapted from an X-ray powder diffractometer assembly and providing a monochromatic X-ray beam having an adjustable wavelength, comprising:

X-ray means for providing a source X-ray beam wherein said X-ray means is fixed with respect to said diffractometer assembly;

a monochromator crystal means rotatably positioned at the center of said X-ray diffractometer assembly to diffract said source X-ray beam to provide a monochromatic X-ray beam associated with selected angles of incidence of said source X-ray beam with respect to said crystal means, said crystal means producing a different wavelength upon changing to a different respective associated one of said angles of incidence;

deforming means for automatically and elastically distorting said monochromator crystal means at each of said angles of incidence to provide said monochromatic X-ray beam having said different wavelength at each of said respective associated angles; and stage means for holding a specimen for irradiation by said monochromatic X-ray beam.

40. The apparatus of claim 39 further including detector means coupled to said stage means for detecting said X-ray beam after irradiation of said specimen.

* * * * *